United States Patent
Chang et al.

(10) Patent No.: US 6,890,906 B2
(45) Date of Patent: May 10, 2005

(54) METHOD FOR CONTROLLING ANGIOGENESIS IN ANIMALS

(75) Inventors: Yan Chang, Ashland, MA (US); Vodek Sasak, Northboro, MA (US)

(73) Assignee: Glycogenesys, Inc., Boston, MA (US)

( * ) Notice: Subject to any disclaimer, the term of this patent is extended or adjusted under 35 U.S.C. 154(b) by 0 days.

(21) Appl. No.: 10/299,478

(22) Filed: Nov. 19, 2002

(65) Prior Publication Data

US 2003/0100535 A1 May 29, 2003

Related U.S. Application Data

(60) Provisional application No. 60/331,793, filed on Nov. 21, 2001.

(51) Int. Cl.[7] .................. A61K 31/70; A61K 31/715; C08B 37/06
(52) U.S. Cl. ................. 514/23; 514/25; 514/53; 514/54; 536/2; 536/1.11; 536/4.1; 536/123; 536/123.1
(58) Field of Search .............. 514/23, 25, 53, 514/54; 536/2, 1.11, 4.1, 123.1, 123

(56) References Cited

U.S. PATENT DOCUMENTS

| | | | |
|---|---|---|---|
| 5,834,442 A | 11/1998 | Raz et al. | 514/54 |
| 5,895,784 A | 4/1999 | Raz et al. | 514/54 |
| 6,258,383 B1 | 7/2001 | Gohlke et al. | |
| 6,423,314 B2 | 7/2002 | Platt | 424/184.1 |
| 6,500,807 B1 | 12/2002 | Platt et al. | |
| 6,632,797 B2 * | 10/2003 | Siren | 514/23 |
| 6,680,306 B2 | 1/2004 | Chang et al. | |
| 2001/0031744 A1 * | 10/2001 | Kosbab | 514/54 |

OTHER PUBLICATIONS

Makker et al.; "Galectin–3 Induces Endothelial Cell Morphogenesis and Angiogenesis", Am. Journal of Pathology, vol. 156, No. 3, Mar. 2000.

Pienta, et al., Inbhibition of Spontaneous Metastasis In a Rat Prostate Cancer Model by Oral Administration of Modified Citrus Pectin, Journal of the National Cancer Institute, vol. 87, No. 5, Mar. 1, 1995, pp. 348–353.

Platt, Modulation of the Lung Colonization of B16–F1 Melanoma Cells by Citrus Pectin, Journal of the National Cancer Institute, vol. 84, No. 6, Mar. 18, 1992, pp. 438–442.

* cited by examiner

*Primary Examiner*—James O. Wilson
*Assistant Examiner*—Everett White
(74) *Attorney, Agent, or Firm*—Ropes & Gray LLP

(57) ABSTRACT

Disease conditions which are dependent upon or moderated by angiogenesis are controlled by the use of a therapeutic material which interacts with cell surface galectins. Particular therapeutic materials comprise a polymeric backbone having side chains terminating in a sugar dependent therefrom. Disclosed are specific therapeutic materials in which the polymeric backbone is based upon polygalacturonic acid, and the side chains terminate in arabinose or galactose.

26 Claims, No Drawings

METHOD FOR CONTROLLING ANGIOGENESIS IN ANIMALS

RELATED APPLICATION

This application claims priority of U.S. Provisional Patent Application Ser. No. 60/331,793 filed Nov. 21, 2001, entitled "Method for Controlling Angiogenesis in Animals."

FIELD OF THE INVENTION

This invention relates to methods and compositions for controlling angiogenesis in an animal. More particularly, the present invention relates to materials and methods for the treatment of diseases in which angiogenesis is a factor. Most specifically, the invention relates to methods and materials for controlling angiogenesis by the use of compounds which interact with galectins.

BACKGROUND OF THE INVENTION

Medical science has recognized that angiogenesis is an important factor in the initiation and/or proliferation of a large number of diverse disease conditions. As used herein, the term "angiogenesis" means the generation and growth of new blood vessels into a tissue or organ. Under normal physiological conditions, humans and other animals only undergo angiogenesis in very specific, restricted situations. For example, angiogenesis is normally observed in wound healing, fetal and embryonic development, and in the formation of the corpus luteum, endometrium and placenta. The process of angiogenesis has been found to be altered in a number of disease states, and in many instances, the pathological damage associated with the disease is related to uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating new blood vessels. Creation of the new microvascular system can initiate or exacerbate disease conditions.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases and conditions associated with corneal neovascularization include, but are not limited to, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson disease, pemphigoid, radial keratotomy, and corneal graft rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogeneic-related factors contributes to the destruction of the joint. At a later stage, the angiogeneic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means can lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula, thereby preventing conception.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Clearly, the development and progress of many disease conditions can be controlled by controlling the process of angiogenesis. In that regard, the art has made many attempts to develop materials and therapies which are capable of controlling angiogenesis. However, many materials which appear promising in vitro have proven to be relatively ineffective when applied in vivo. Furthermore, various of such materials have been found to be unstable, toxic, or otherwise difficult to employ. Consequently, there is a need for methods and materials capable of controlling angiogenesis in a reliable manner.

The present invention recognizes that galectins play a significant role in moderating angiogenesis. The invention further recognizes that compounds which interact with galectins can control disease conditions in which angiogenesis plays a role.

BRIEF DESCRIPTION OF THE INVENTION

There is disclosed herein a method for controlling angiogenesis in an organism. The method comprises the step of administering to the organism a therapeutically effective amount of a compound which binds to a galectin. In specific embodiments, the therapeutically effective compound comprises a substantially demethoxylated polygalacturonic acid which is interrupted with rhamnose residues. In other instances, the compound may be characterized as a polymeric backbone having side chains dependent therefrom which side chains are terminated by a galactose or arabinose unit. In specific instances, the compound comprises a modified pectin, and particular modified pectins comprise pH modified pectin, enzymatically modified pectin or thermally modified pectin.

The therapeutically effective compound may be administered orally, transdermally, topically or by injection.

In particular embodiments, the therapeutic treatment of the present invention is directed to diseases which are dependent upon neovascularization. The invention also includes compounds for controlling angiogenesis in an animal. These compounds include a first functional portion which is operable to bind to the carbohydrate binding side of a galectin, and a second functional portion which is operable to denature a protein.

DETAILED DESCRIPTION OF THE INVENTION

The present invention recognizes the role of galectins in angiogenesis, and provides a therapeutic material which will advantageously interact with galectins so as to moderate or prevent the manifestations of angiogenesis-dependent disease. Specifically, the present invention recognizes that particular carbohydrate materials will bind to or otherwise interact with galectins and thereby modify their interaction with cellular structures, and thereby control angiogenesis.

Galectins comprise a family of proteins which are expressed by plant and animal cells, and which bind β-galactoside sugars. These proteins can be found on cell surfaces, in cytoplasm, and in extracellular fluids. They have a molecular weight in the general range of 29–34 kd; they have an affinity for β-galactoside containing materials, and have been found to play important roles in a number of biological processes. Galectin-1 and galectin-3 are specific members of this family which have been found to interact with various cellular structures, and galectin-3 has been demonstrated to promote angiogenesis in vitro.

While galectins are known to bind galactose and other such simple sugars in vitro, those simple sugars are not therapeutically effective in moderating angiogenesis in vivo. While not wishing to be bound by speculation, the inventors hereof presume that such relatively small sugar molecules are incapable of blocking, activating, suppressing, or otherwise interacting with other portions of the galectin protein.

Therefore, preferred materials for the practice of the present invention generally comprise molecules which contain an active galectin binding sugar site, but which have somewhat higher molecular weights than simple sugars. Such molecules preferably have a minimum molecular weight of at least 300 daltons, and most typically a minimum molecular weight in the range of 300–2,000 daltons. Some specifically preferred materials have yet higher molecular weight ranges.

A preferred class of therapeutic materials comprises oligomeric or polymeric species having one or more sugars such as galactose or arabinose pendent therefrom. The oligomeric or polymeric backbone may be synthetic or organic. Materials of this type are disclosed in U.S. Pat. No. 6,423,314 the disclosure of which is incorporated herein by reference. Such materials will preferably have a molecular weight in the range of 300–50,000 daltons. It should be kept in mind that there is some inherent uncertainty in molecular weight measurements of high molecular weight carbohydrates, and measured molecular weights will be somewhat dependent on the method used for measuring the molecular weight. Molecular weights given herein are based on viscosity measurements, and such techniques are known in the art.

One group of materials falling within this general class comprises a substantially demethoxylated polygalacturonic acid backbone having rhamnose residues pendent therefrom. It is believed that in materials of this type, the terminal galactose or arabinose units pendent from the backbone bind to galectin proteins. The remaining bulk of the molecule potentiates the compound's action in moderating immune system response, and as discussed hereinabove, the inventors, while not wishing to be bound by speculation, believe that the remaining bulk of the molecule either interacts with remaining portions of the galectin protein and/or prolongs the binding of the sugar portion thereto. Materials of this general type are described by formulas I–V hereinbelow, and it is to be understood that yet other variants of this general compound may be prepared and utilized in accord with the principles of the present invention.

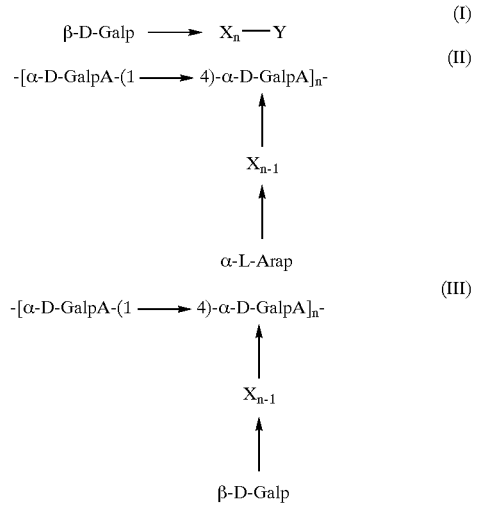

where n≧1.

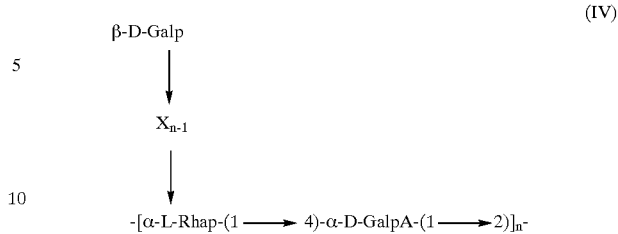

where n≧1.

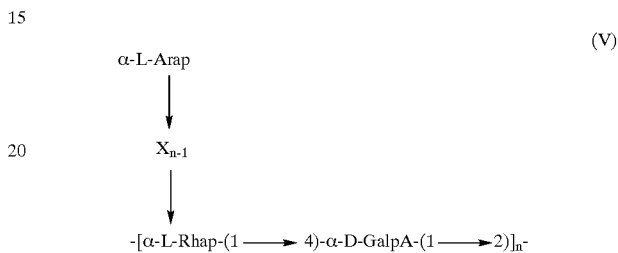

where n≧1.

Pectin is a complex carbohydrate having a highly branched structure comprised of a polygalacturonic backbone with numerous branching side chains dependent therefrom. The branching creates regions which are characterized as being "smooth" and "hairy." It has been found that pectin can be modified by various chemical, enzymatic or physical treatments to break the molecule into smaller portions having a more linearized, substantially demethoxylated polygalacturonic backbone with pendent side chains of rhamnose residues having decreased branching. This material is known in the art as modified pectin, and its efficacy in treating cancer has been established. U.S. Pat. No. 5,895,784, the disclosure of which is incorporated herein by reference, describes modified pectin materials, techniques for their preparation, and use of the material as a treatment for various cancers. The material of the '784 patent is described as being prepared by a pH based modification procedure in which the pectin is put into solution and exposed to a series of programmed changes in pH which results in the breakdown of the molecule to yield therapeutically effective modified pectin. The material in the '784 patent is most preferably prepared from citrus pectin; although, it is to be understood that modified pectins may be prepared from pectin starting material obtained from other sources, such as apple pectin and the like. Also, modification processes may be accomplished by enzymatic treatment of the pectin, or by physical processes such as heating. Further disclosure of modified pectins and techniques for their preparation and use are also disclosed in U.S. Pat. No. 5,834,442 and U.S. patent application Ser. No. 08/024,487, the disclosures of which are incorporated herein by reference. Modified pectins of this type generally have molecular weights in the range of 1–50 kilodalton, and a preferred group of such materials has an average molecular weight of about 1–15 kilodalton, and one specific group of materials has a molecular weight of approximately 10 kilodalton. Another preferred group of such materials has a molecular weight in the range of 15–60 kd, with a particular group of these materials having a molecular weight in the range of 20–40 kd, with a particular material having a molecular weight of about 25 kd.

As disclosed in the prior art, such modified pectin materials have therapeutic efficacy against a variety of cancers. These materials interact with galectins, including galectin-1 and galectin-3, and in that regard also have efficacy in controlling diseases and conditions in which angiogenesis is a factor. In accord with the present invention, angiogenesis can be controlled or moderated by the use of modified pectin materials and other materials which interact with galectins. These materials may be administered orally; or by intravenous injection; or by injection directly into an affected tissue, as for example by injection into an arthritic joint. In some instances the materials may be administered topically, as in the form of eye drops, nasal sprays, ointments or the like. Also, other techniques such as transdermal delivery systems, inhalation or the like may be employed.

While the foregoing discussion has been primarily directed to therapeutic materials based upon modified pectins, it is to be understood that the present invention is not so limited. In accord with the general principles of the present invention, any member of the broad class of compounds which can interact with and block galectins may be employed to treat immune moderated diseases. These materials, in a preferred embodiment, comprise carbohydrate materials, since such materials are low in toxicity and exhibit strong interaction with galectins. Modified pectin materials comprise one particularly preferred group of carbohydrate materials. Likewise, synthetic and semi-synthetic analogs thereof such as polygalacturonic acid materials may be similarly employed.

Yet another class of materials of the present invention comprises molecules which have a first portion, which is typically a carbohydrate, and which is capable of binding to galectins, joined to a second portion which inactivates or otherwise moderates the activity of a protein. This second portion need not be a carbohydrate and can comprise a material which cross links or otherwise denatures the segment of protein comprising an active portion of the galectin protein, or an active portion of another protein which interacts with the galectin. Such materials include active species such as sulfur or other chalcogen elements alone or in combination such as thiols, sulfhydryls and the like. Other active species may comprise cyano groups, thiocyanates, alkylating agents, aldehydes and the like.

The compounds described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441–446 (1991).

The dosage of the compound will depend on the condition being treated, the particular compound, and other clinical factors such as weight and condition of the patient and the route of administration of the compound. It is to be understood that the present invention has application for both human and veterinary use. For oral administration to humans, a dosage of between approximately 0.1 to 450 mg/kg/day, preferably between approximately 0.5 and 50 mg/kg/day, and most preferably between approximately 1 to 20 mg/kg/day, is generally sufficient.

The formulations include those suitable for oral, rectal, ophthalmic (including intravitreal or intracameral), nasal, topical (including buccal and sublingual), vaginal or parenteral (including subcutaneous, intramuscular, intravenous, intradermal, intratracheal and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as hereinabove recited, or an appropriate fraction thereof, of the administered ingredient.

It should be understood that in addition to the ingredients particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical bums, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, and corneal graft rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease is active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are hemangiomas, Osler-Weber-Rendu disease, or hereditary hemorrhagic telangiectasia, solid or blood borne tumors and acquired immune deficiency syndrome.

The principles of the present invention are illustrated in an experimental series which assesses the effect of a therapeutic carbohydrate material of the present invention, in inhibiting the process of angiogenesis.

Chemotaxis is an integral part of angiogenesis, and this experimental series demonstrates the effect of a modified pectin material of the present invention in inhibiting angiogenesis. In a first portion of the experimental series, the effect of the chemoattractant vascular endothelial growth factor (VEGF) on human umbilical vein endothelial cells (HUVEC) was quantified. The experiment was carried out in a transwell plate, and in preparation therefor, HUVEC cells were grown to approximately 80% confluency. The cells were suspended in basal media and placed in a transwell plate on fibronectin coated membrane inserts at 50,000 cells per insert. Varying concentrations of VEGF were added to the bottom chamber of the transwell plate, and the plates incubated for 4 hours at 37° C. with a 5% $CO_2$ atmosphere. Following incubation, the membranes were fixed and stained. Nonmigrated cells were removed by mechanical abrasion and cells that migrated through the membrane were counted. Data from this first experiment is shown in FIG. 1. As will be seen, VEGF is a chemotactic agent which induces cell migration, which process is crucial to angiogenesis. Based upon the first experimental series, it was found that VEGF concentrations of 10–30 ng/ml produce a strong chemotactic effect. Three runs were made. Data from the experiment is summarized in Table 1 hereinbelow.

TABLE 1

| Samples | NEG. | 1 ng/ml VEGF | 3 ng/ml VEGF | 10 ng/ml VEGF | 30 ng/ml VEGF | 100 ng/ml VEGF |
|---|---|---|---|---|---|---|
| Cell count | 123 | 607 | 950 | 1144 | 898 | 1650 |
| Cell count | 300 | 766 | 1136 | 938 | 1448 | 901 |
| Cell count | 250 | 830 |  | 1573 | 1140 | 1078 |
| AVERAGE | 224 | 734 | 1043 | 1218 | 1162 | 1210 |

In a second portion of the experiment, the effect of a therapeutic carbohydrate material of the present invention, in moderating chemotaxis, and hence angiogenesis, was evaluated. The material comprised a modified pectin which is commercially available from GlycoGenesys, Inc. of Boston, Mass., under the designation GCS-100. In this experimental series, HUVEC cells were incubated in a transwell plate with VEGF, and varying concentrations of the therapeutic material, under conditions as described hereinabove. The concentration of VEGF was 30 ng/ml. In one group of experiments, cells were incubated with VEGF in the absence of the carbohydrate material, and these experiments served as a positive control. In another group of experiments, cells were incubated with growth medium and no VEGF or therapeutic carbohydrate, and this group served as a negative control. In the remaining experiments, concentrations of the GCS-100 ranging from 0.001% to 0.1% were employed. The data from this experimental series is summarized in Table 2 hereinbelow.

As will be seen, the GCS-100 material strongly inhibited cell migration, and the inhibition is concentration dependent. As established by this experimental series, the GCS-100 material is a potent inhibitor of the angiogenic process, and as such will have utility in the treatment of diseases in which angiogenesis is a factor. The GCS-100 material is known to bind to galectins which are found on the surface of cells such as HUVEC cells; therefore, other such carbohydrate materials which bind to galectins will be expected to exert a similar effect in inhibiting cell migration and angiogenesis.

The foregoing is illustrative of particular embodiments and features of the present invention. In view of the teaching presented herein, one of skill in the art could readily prepare and select other materials for use in controlling angiogenesis and disease conditions. The foregoing drawings, disclosure, examples and discussion are not limiting upon the present invention but are illustrative of the principles thereof. It is the following claims, including all equivalents, which define the scope of the invention.

What is claimed is:

1. A method for controlling angiogenesis in an organism, said method comprising administering to said organism a therapeutically effective amount of a compound which binds to a galectin, said compound comprising a polymeric backbone which is a partially demethoxylated polygalacturonic acid interrupted with rhamnose residues.

2. The method of claim 1, wherein said galectin is present on the cell surface of a tissue of said organism.

3. The method of claim 1, wherein said compound binds to galectin-1 or galectin-3.

4. The method of claim 1, wherein said compound comprises a polymeric backbone having a side chains dependent from said backbone, said side chains comprising one or more sugars and being terminated by a galactose or arabinose unit.

5. The method of claim 1, wherein said compound comprises a modified pectin.

6. The method of claim 5, wherein said modified pectin comprises a pH modified pectin.

7. The method of claim 5, wherein said modified pectin comprises an enzymatically modified pectin.

8. The method of claim 5, wherein said modified pectin comprises a thermally modified pectin.

9. The method of claim 5, wherein said modified pectin comprises a modified citrus pectin.

10. The method of claim 5, wherein said modified pectin has a molecular weight in the range of 1–50 kilodalton.

11. The method of claim 5, wherein said modified pectin has a molecular weight in the range of 25–40 kilodalton.

12. The method of claim 5, wherein the modified pectin has a molecular weight of approximately 25 kilodalton.

13. The method of claim 5, wherein said modified pectin has a molecular weight of approximately 10 kilodalton.

TABLE 2

| Samples | VEGF 30 ng/ml Only | Medium Only | VEGF 30 ng/ml GCS-100 0.001% | VEGF 30 ng/ml GCS-100 0.005% | VEGF 30 ng/ml GCS-100 0.01% | VEGF 30 ng/ml GCS-100 0.05% | VEGF 30 ng/ml GCS-100 0.1% |
|---|---|---|---|---|---|---|---|
| Cell count | 1322 | 208 | 841 | 750 | 463 | 364 | 271 |
| Cell count | 1167 | 346 | 819 | 539 | 412 | 594 | 222 |
| Cell count |  |  | 548 | 655 |  | 430 | 170 |
| AVERAGE | 1244 | 277 | 736 | 648 | 437 | 463 | 221 |

14. The method of claim 5, wherein said modified pectin has a molecular weight in the range of 15–60 kilodalton.

15. The method of claim 1, wherein said compound has a molecular weight of at least 300 dalton.

16. The method of claim 1, wherein administering said compound to said organism comprises injecting said compound into said organism.

17. The method of claim 1, wherein administering said compound to said organism comprises topically applying said compound to said organism.

18. The method of claim 1, wherein administering said compound to said organism comprises administering said compound transdermally.

19. The method of claim 1, wherein administering said compound to said organism comprises orally administering said compound.

20. A method for the therapeutic treatment of a disease in an animal, the progress of which disease is dependent upon neovascularization in the tissues of said animal, said method comprising: administering to said animal a therapeutically effective amount of a compound which binds to a galectin, said compound comprising a polymeric backbone which is a partially demethoxylated polygalacturonic acid interrupted with rhamnose residues; whereby said compound decreases the rate of angiogenesis and neovascularization in said tissues.

21. The method of claim 20, wherein said compound binds to galectin-1 or galectin-3.

22. The method of claim 20, wherein said compound further comprises a side chains dependent from said backbone, said side chains comprising one or more sugars and being terminated by a galactose or arabinose unit.

23. The method of claim 20, wherein said compound comprises a modified pectin.

24. A method for controlling angiogenesis in an organism, said method comprising:
    administering to said organism a therapeutically effective amount of modified pectin.

25. The method of claim 24, wherein the modified pectin is thermally modified pectin.

26. The method of claim 24, wherein the modified pectin is pH-modified pectin.

* * * * *

UNITED STATES PATENT AND TRADEMARK OFFICE
CERTIFICATE OF CORRECTION

PATENT NO. : 6,890,906 B2 Page 1 of 1
APPLICATION NO. : 10/299478
DATED : May 10, 2005
INVENTOR(S) : Yan Chang et al.

It is certified that error appears in the above-identified patent and that said Letters Patent is hereby corrected as shown below:

In the claims:

Claim 4, col. 12, line 31, delete "a polymeric backbone having"; and delete "chains" and instead insert --chain--;

Claim 4, Col. 12, line 32, delete "chains" and instead insert --chain--;

Claim 22, Col. 14, line 7, delete "chains" and instead insert --chain--; and

Claim 22, Col. 14, line 8, delete "chains" and instead insert --chain--.

Signed and Sealed this

Second Day of October, 2007

JON W. DUDAS
*Director of the United States Patent and Trademark Office*

(12) INTER PARTES REEXAMINATION CERTIFICATE (0011th)
United States Patent
Chang et al.

(10) Number: US 6,890,906 C1
(45) Certificate Issued: Sep. 25, 2007

(54) METHOD FOR CONTROLLING ANGIOGENESIS IN ANIMALS

(75) Inventors: Yan Chang, Ashland, MA (US); Vodek Sasak, Northboro, MA (US)

(73) Assignee: Glycogenesys, Inc., Boston, MA (US)

Reexamination Request:
No. 95/000,176, Sep. 6, 2006

Reexamination Certificate for:
Patent No.: 6,890,906
Issued: May 10, 2005
Appl. No.: 10/299,478
Filed: Nov. 19, 2002

Related U.S. Application Data
(60) Provisional application No. 60/331,793, filed on Nov. 21, 2001.

(51) Int. Cl.
*A61K 31/00* (2006.01)
*A61K 31/732* (2006.01)
*A61K 31/715* (2006.01)

(52) U.S. Cl. ............... 514/23; 514/25; 514/53; 514/54; 536/2; 536/1.11; 536/4.1; 536/123; 536/123.1

(58) Field of Classification Search ............ None
See application file for complete search history.

(56) References Cited

U.S. PATENT DOCUMENTS

| | | | |
|---|---|---|---|
| 5,484,951 A | * | 1/1996 | Kun et al. ............ 549/285 |
| 5,834,442 A | | 11/1998 | Raz et al. |
| 5,895,784 A | | 4/1999 | Raz et al. |

FOREIGN PATENT DOCUMENTS

EP 0888366 B1 6/2004

* cited by examiner

*Primary Examiner*—Bennett M. Celsa

(57) ABSTRACT

Disease conditions which are dependent upon or moderated by angiogenesis are controlled by the use of a therapeutic material which interacts with cell surface galectins. Particular therapeutic materials comprise a polymeric backbone having side chains terminating in a sugar dependent therefrom. Disclosed are specific therapeutic materials in which the polymeric backbone is based upon polygalacturonic acid, and the side chains terminate in arabinose or galactose.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1–26 are cancelled.

\* \* \* \* \*